(12) United States Patent
Ewing et al.

(10) Patent No.: US 8,245,564 B1
(45) Date of Patent: Aug. 21, 2012

(54) CHEMICAL SAMPLE COLLECTION AND DETECTION SYSTEM

(75) Inventors: Kenneth J. Ewing, Elkridge, MD (US); Fred Whiton, Jr., Towson, MD (US); Paul G. Kahl, Jr., Perry Hall, MD (US)

(73) Assignee: Northrop Grumman Systems Corporation, Falls Church, VA (US)

( * ) Notice: Subject to any disclaimer, the term of this patent is extended or adjusted under 35 U.S.C. 154(b) by 975 days.

(21) Appl. No.: 12/232,359

(22) Filed: Sep. 16, 2008

(51) Int. Cl.
*G01N 7/00* (2006.01)
(52) U.S. Cl. ..................................... 73/31.02
(58) Field of Classification Search .............. 73/31.01, 73/31.02, 31.05, 31.07, 863, 863.11, 863.12, 73/861.21–861.23
See application file for complete search history.

(56) References Cited

U.S. PATENT DOCUMENTS

| | | | | |
|---|---|---|---|---|
| 4,414,857 A | * | 11/1983 | Brazhnikov et al. | 73/863.11 |
| 5,092,156 A | * | 3/1992 | Miskolczy | 73/863.12 |
| 5,092,157 A | * | 3/1992 | Achter et al. | 73/863.12 |
| 5,092,219 A | * | 3/1992 | Rounbehler et al. | 86/50 |
| 5,123,274 A | * | 6/1992 | Carroll et al. | 73/863.12 |
| 5,162,652 A | * | 11/1992 | Cohen et al. | 250/288 |
| 5,259,254 A | * | 11/1993 | Zhu et al. | 73/864.81 |
| 5,345,809 A | * | 9/1994 | Corrigan et al. | 73/23.2 |
| 5,465,607 A | * | 11/1995 | Corrigan et al. | 73/23.36 |
| 5,585,575 A | * | 12/1996 | Corrigan et al. | 73/863.71 |
| 5,760,314 A | * | 6/1998 | Bromberg et al. | 73/863.21 |
| 5,798,945 A | * | 8/1998 | Benda | 702/24 |
| 5,922,106 A | * | 7/1999 | Mowry et al. | 95/87 |
| 7,047,829 B2 | * | 5/2006 | Napoli | 73/864.31 |
| 7,460,225 B2 | * | 12/2008 | Karanassios | 356/316 |
| 7,874,198 B2 | * | 1/2011 | Groves | 73/31.01 |
| 2006/0285108 A1 | * | 12/2006 | Morrisroe | 356/316 |
| 2009/0101814 A1 | * | 4/2009 | Amirav | 250/288 |

* cited by examiner

*Primary Examiner* — John Fitzgerald
(74) *Attorney, Agent, or Firm* — Andrews Kurth LLP

(57) ABSTRACT

A system for remote detection of a chemical is disclosed. The system includes a sample collection module that collects a sample and produces a sample vapor at a first location; a sample delivery module that delivers the sample vapor from the first location to a second location; a sample storage and concentration module that collects the sample vapor at the second location; and a sample analysis module that analyzes the sample collected in the sample storage and concentration module.

20 Claims, 14 Drawing Sheets

CHEMICAL SAMPLE COLLECTION AND DETECTION SYSTEM

TECHNICAL FIELD

The invention relates generally to detection systems, and more particularly, to a system capable of remote detection of chemicals.

BACKGROUND

In recent years, there has been a demand for devices capable of detecting dangerous chemicals, such as chemical warfare agents, explosives, and toxic industrial chemicals, from a safe distance. Ideally, such devices should be able to collect both solid and liquid aerosols, as well as vapors, from a remote site and analyze the collected materials for the presence of the chemicals of interest. Since the chemicals of interest may be present at a very low concentration (e.g., on the order of parts per billion (ppb) or less), such devices need to be highly sensitive with low false positive and false negative rates.

SUMMARY

A system for remote detection of a chemical and aerosol is disclosed. The system includes a sample collection module that collects a vapor and aerosol sample and produces a sample vapor at a first location; a sample delivery module that delivers the sample vapor from the first location to a second location; a sample storage and concentration module that collects the sample vapor at the second location; and a sample analysis module that analyzes the sample collected in the sample storage and concentration module.

Also disclosed is a method for detecting a chemical at a remote site. The method includes the steps of collecting vapors, aerosols, and particles from a fluid sample at a remote site; heating the collected vapors, aerosols and particles to produce a sample vapor; transporting the sample vapor over a distance to a sample storage and concentrating device; absorbing the transported sample vapor in an absorbent in the sample storage and concentrating device; desorbing the absorbed sample vapor, and analyzing the desorbed sample vapor for the presence of said chemical.

DETAILED DESCRIPTION OF DRAWINGS

FIG. 1 is a schematic of an embodiment of a chemical sample collection and detection system.

FIG. 2 is a diagram showing working cycles of the sorbent tubes in a storage and concentration module.

FIG. 3 is a flow chart showing a method for detecting chemicals.

FIG. 4 is a diagram showing two configurations used for CSCDS testing.

FIG. 5 is a diagram showing LoVac signal for 10 ng of dimethoate.

FIG. 6 is a diagram showing LoVac signal for 3,880 ng of methamidophos.

FIG. 7 is a diagram showing LoVac signal for 1,000 ng of acephate.

FIG. 8 is a diagram showing sample introduction setup for testing the CSCDS capability to detect simulant aerosol.

FIG. 9 is a diagram showing LoVac response to dimethoate/Celite sample.

FIG. 10 is a diagram showing LoVac response to acephate/Celite sample.

FIG. 11 is a diagram showing CSCDS response to 250 ng of dimethoate through the 3 foot long silcosteel HSTL. The concentration of dimethoate is 11 ppb.

FIG. 12 is a diagram showing CSCDS response to 1.83 ug of dimethoate through the 10 foot long silcosteel HSTL. The concentration of dimethoate is 195 ppb.

FIG. 13 is a diagram showing CSCDS response to 6 ug of acephate through the 10 foot long silcosteel HSTL. The concentration of acephate is 800 ppb.

FIG. 14 is a diagram showing CSCDS response to 46 ug of methamidophos through the 10 foot long silcosteel HSTL. The concentration of acephate is 800 ppb.

DETAILED DESCRIPTION

FIG. 1 schematically shows an embodiment of a system for remote detection of a chemical of interest. As shown in FIG. 1, the chemical sample collection and detection system 100 includes four primary modules: a sample collection module 110, a sample transport module 120, a sample storage and concentration module 130, and a sample detection module 140. These primary modules are combined with additional supporting modules such as command and control module 150, communications module 160 and power module 170 to form a complete system. The chemical sample collection and detection system 100 can be used to detect trace amount of the chemicals of interest.

The "chemicals of interest" can be any chemicals. Examples include, but not limited to, chemical warfare agents (CWA), non-traditional agents (NTAs), dusty agents (DAs), toxic industrial chemical (TIC) vapors, low vapor pressure chemicals (LVPCs), explosives, explosives and their related compounds, and residues thereof.

Examples of CWA includes, but are not limited to, nerve agents such as GA (Tabun, ethyl N,N-dimethyl phosphoramidocyanidate), GB (Sarin, isopropyl-methylphosphorofluoridate), GD (Soman, Trimethylpropylmethylphosphorofluoridate), GF (cyclohexyl-methylphosphorofluoridate) and VX (o-ethyl S-[2-(diiospropylamino)ethyl]methylphosphorofluoridate); vesicants such as HD (mustard, bis-2-chlorethyl sulfide), CX (Phosgene oxime, dichloroformoxime), and L (Lewisite, J-chlorovinyldichloroarsine); cyanides such as AC (Hydrocyanic acid) and CK (Cyanogen chloride); pulmonary agents such as CG (phosgene, carbonyl chloride) and DP (Diphosgene, trichloromethylchlorformate).

NTAs and DAs are CWAs dispersed as either a liquid or particulate aerosol. For example, dusty mustard is composed of mustard agent (liquid) dispersed onto fine particulates of silica.

Examples of TIC can be found on U.S. Environmental Protection Agency's reference list of toxic compounds (Alphabetical Order List of Extremely Hazardous Substances" Section 302 of EPCRA).

The term "LVPCs" refers to those chemicals that, at atmospheric temperature and pressure, only an intangible level, if any, of the sample exists in the gaseous and/or vapor phase and as such the sample has, at atmospheric temperature and pressure, a vapor pressure significantly less than water.

Examples of LVPCs include, but are not limited to, Novichock agents, dusty agents, pesticides, and other toxic chemicals with vapor pressures less than $10^{-4}$ torr.

Examples of explosives include, but are not limited to, nitroglycerin-based powders, ammonium nitrate/fuel oil mixtures (ANFO), Trinitrotoluene (TNT), Pentaerythritoltetranitrate (PETN), Cyclotrimethylenetrinitramine (RDX), and Cyclotetramethylene-tetranitramine (HMX). Explosive related compounds include, but are not limited to, residual raw materials, manufacturing byproducts and degradation products.

For the purposes of this disclosure, a residue is considered to be a small amount of a substance, or a material associated with that substance. A residue may not directly be the substance whose detection is desired, but may be a substance indicative of the presence of the first substance. For instance, a residue of a chemical agent may be a degradation product of the chemical agent, a chemical binder used to particulate a gaseous CWA, or a substrate on which a CWA is placed.

As used herein, the term "remote detection" shall be taken to mean that the sample of the chemical of interest is taken at a location that is different from the location of the sample detection module 140 or the location of the operator of the detection system.

As used herein, the term "vaporize" shall be taken to mean that at least some of the sample has been converted to a vapor.

Sample Collection Module

Figure 1:
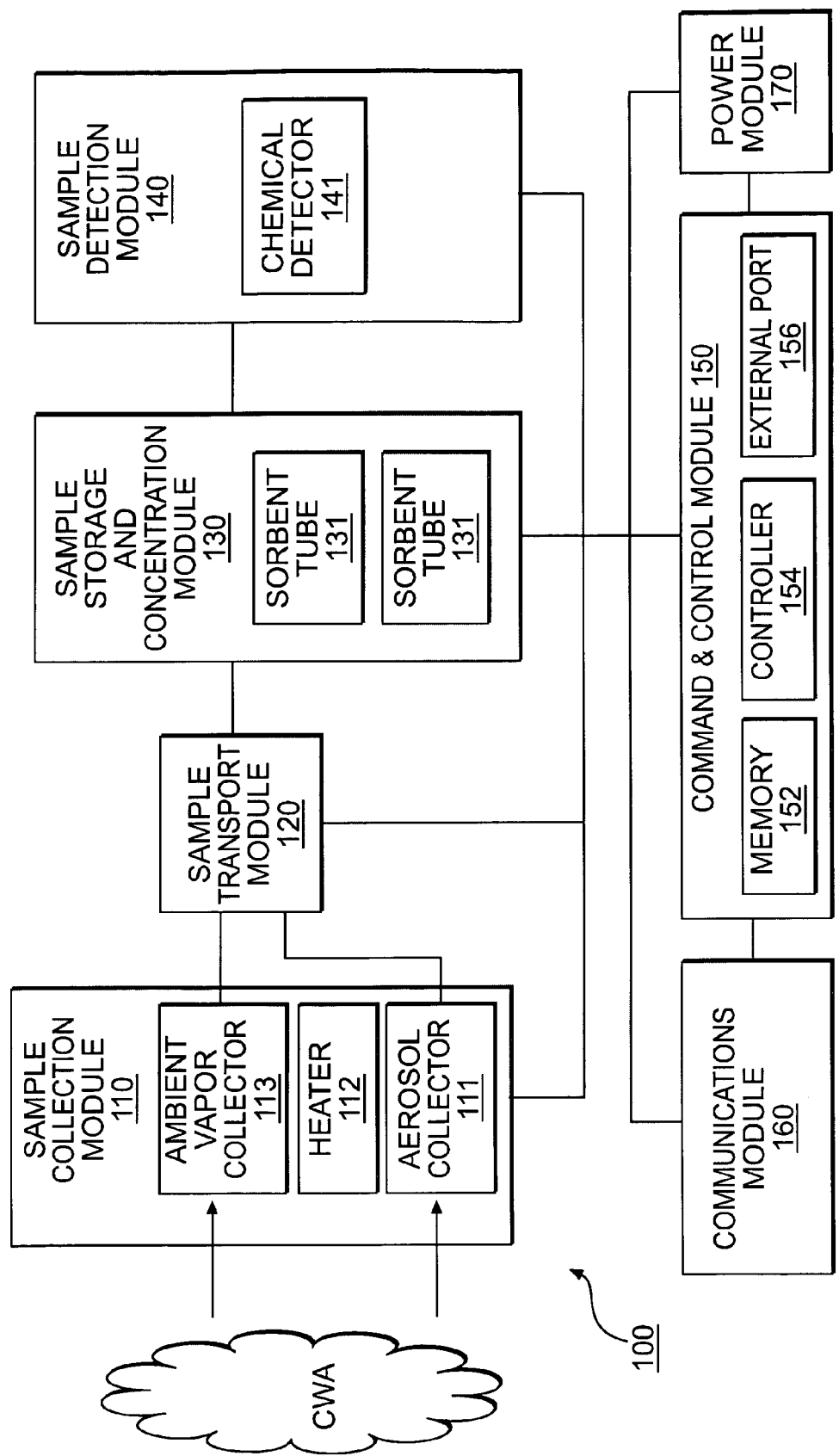

With continued reference to FIG. 1, the sample collection module 110 collects aerosols, particles and vapors from a sample fluid and prepares the collected materials for transport. As used in embodiments described herein, the term "aerosol" refers to a suspension of fine solid or liquid droplets in a gas, such as ambient air. The term "vapor" on the other hand, refers to the gas phase of a liquid or solid material. The aerosols are collected through the use of an aerosol collector 111. The term "fluid," as used in the embodiments described herein after, refers to a substance that continually deforms (flows) under an applied shear stress regardless of how small the applied stress. Fluids are a subset of the phases of matter and include liquids, gases, aerosols (particles in a gas stream), plasmas and, to some extent, solids.

In one embodiment, the aerosol collector 111 is designed to capture aerosols in the respirable size range (1 to 10 µm).

The aerosol collector 111 can be a commercial off-the-shelf particle/aerosol collector or a collector specifically designed for the chemical agent detection system 100. Examples of the aerosol collector 111 include, but are not limited to, electrostatic collectors, virtual impactors, regular plate impactors, cyclone separators and filter-based collectors.

In one embodiment, the aerosol collector 111 is an electrostatic collector. The electrostatic collector removes particles from an air sample by using electrostatics to direct the particles or aerosols onto a metal grid or into a liquid, creating a highly concentrated particle/aerosol sample.

In another embodiment, the aerosol collector 111 is a virtual impactor with a desired threshold size. Briefly, a jet of particle-laden air is accelerated toward a collection probe positioned downstream so that a small gap exists between the acceleration nozzle and the probe. A vacuum is applied to deflect a major portion of the airstream through the small gap. Particles larger than a preset threshold size, known as the cutpoint, have sufficient momentum so that they cross the deflected streamlines and enter the collection probe, whereas smaller particles follow the deflected airstream. Larger particles are removed from the collection probe by the minor portion of the airstream according to the magnitude of the vacuum applied to the minor portion.

In another embodiment, the aerosol collector 111 is a regular impactor. The particles are accelerated through a nozzle towards an impactor plate maintained at a fixed distance from the nozzle. The plate deflects the flow creating fluid streamlines around itself. Due to inertia, the larger particles are impacted (and collected) on a collector plate while the smaller particles follow the deflected streamlines.

In another embodiment, the aerosol collector 111 is a cyclone separator. Cyclone separators separate particle/aerosol from gas streams using centrifugal force. In a typical cyclone, the sample gas stream enters at an angle and is spun rapidly. The centrifugal force created by the circular flow throws the particles in the gas stream toward the wall of the cyclone. After striking the wall, these particles fall into a hopper located underneath.

In another embodiment, the aerosol collector 111 is a filter-based collector that collects the explosives or chemical agents on a filter. The filter can be a porous material that traps particles/aerosols.

The sample can be ambient air collected from a region of interest, such as a region with a suspected chemical agent plant or the vicinity of a luggage that may contain an explosive. The sample may also be a liquid sample. The collection conditions, such as the sample flow rate and collecting temperature, may be optimized for the chemical agent of interest.

With continued reference to FIG. 1, the collected aerosols are then converted to a vapor through the controlled heating of the collected material by a heater 112. As the collected material is heated, vapors are given off. In one embodiment, the aerosol collector 111 also possess the capability to "flash" off the aerosol (i.e., evaporate the sample by a rapid increase of temperature), thus delivering a highly concentrated "puff" of vapor to the storage and concentration module 130 or directly to the sample detection system 140. In another embodiment, the aerosol collector 111 is capable of performing self cleaning operation. In one embodiment, the aerosol collection surface of the aerosol collector 111 is heated to the pyrolysis temperature of any collected sample, effectively reducing any remaining sample or contaminants into ashes. The pyrolysis temperature of an organic material is the temperature at which the organic material decomposes, i.e., break down into simpler molecules.

In one embodiment, the ambient vapor collector 113 is capable of collecting chemical vapors. For example, the ambient vapor collector 113 may use a porous sorbent material that is capable of absorbing chemical vapors and aerosols in the ambient air as the ambient air passes through the porous sorbent material. In one embodiment, the sorbent material is coated on a polytetrafluoroethylene or stainless steel mesh. In another embodiment, the sorbent material is coated on the blades of a fan. In yet another embodiment, the sorbent is used in a packed bed design. After the sampling period, collected vapors are removed from the ambient vapor collector 113 by thermal desorption. In one embodiment, the collected vapors are re-vaporized by heating the ambient vapor collector 113 to a vaporizing temperature with the heater 112. The newly generated, concentrated vapor is then combined with the vapor generated from the other collected materials, and sent to the sample storage and concentration module 130 through the sample transfer module 120.

Sample Transport Module

With continued reference to FIG. 1, once in vapor form (which includes vapor from the aerosol collector 111, the vapor collector 113 or both), the sample collected by the sample collection module 110 is transported by the sample transport module 120 to the sample storage and concentration module 130. In one embodiment, the sample transport module 120 uses the heated sample transfer line (HSTL) technology, where the vapors are transported through Teflon® tubing that is maintained at an elevated temperature ranging from 100° F. to 160° F., and preferably at about 130° F. Other types of HSTLs that can be used as the sample transport module include, but are not limited to, HSTLs made of stainless steel, silcosteel, sulfinert stainless steel, and other polymeric or metallic materials. HSTL technology has been demonstrated to efficiently transfer various chemical vapors, such as the chemical warfare agent HD (mustard), over distances up to 60 m. There are a number of possible configurations of sample transport lines. In one embodiment, a single transfer line is used to transfer vapors generated from both the aerosol collector 111 and ambient vapor collector 113. In another embodiment, two entirely separate transfer lines are used. One line is dedicated to the transport of aerosol vapors and the other line is dedicated to ambient vapors.

Sample Storage and Concentration Module

With continued reference to FIG. 1, after the vapors are transported by the sample transfer module 120, the vapors are collected and concentrated by the sample storage and concentration module 130 using sorbent tube technology. The sorbent tubes collect the vapor over a period of time, and then thermally desorbs the vapor for introduction into the sample detection module 140. The collection and concentration of chemical agent vapors, such as the explosive, LVPC, and NTA vapors, will be performed at temperatures where the target vapors are efficiently collected, while vapors of the lighter, more volatile species, such as water, volatile organic compounds (VOCs), and many TICs are deliberately excluded. Thermal desorption of the target vapors is accomplished by controlling the thermal desorption temperature to remove any background interferents prior to thermal desorption of the target vapors into the detector. In one embodiment, two or more parallel sorbent paths are used to allow continuous operation of the chemical agent detector 100 and parallel processing of multiple vapor samples. For example, while a first sorbent tube is undergoing the desorption process, a second sorbent tube is collecting vapor samples from the sample collection module 110. When the second sorbent tube goes into to the desorption process, the first sorbent tube will collect vapor samples from the sample collection module 110. In another embodiment, three sorbent tubes are employed. While a first sorbent tube is collecting vapor samples from the sample collection module 110, the second sorbent tube undergoes the desorption/analysis process, and a third sorbent tube is being cleaned after the desorption/analysis process.

In another embodiment, the chemical agent detector 100 includes multiple sample collection modules 110 located at multiple sites. Vapor and aerosol samples collected by each sample collection modules 110 are sent to the sample storage and concentration module 130 where the samples may be pooled or stored individually for analysis by the detection module 140. In one embodiment, multiple sorbent tubes are used to collect samples from different locations. In another embodiment, vapor samples from different locations are analyzed sequentially with 2 or 3 sorbent tubes. In one embodiment, two sorbent tubes are used in the sample storage and concentration module 130. While a first sorbent tube containing samples from a first site is undergoing the desorption/analysis process, a second sorbent tube is collecting vapor samples from the second site. When the second sorbent tube goes into to the desorption/analysis process, the first sorbent tube will collect vapor samples from another site. The three-tube setting described above may also apply to the analysis of multiple samples from multiple sites.

Alternatively, samples from multiple sites may be pooled first and subjected to a single analysis. If a chemical of interest is detected in the pooled sample, aliquots of the individual samples will be screened to decide the source of the chemical.

Sample Detection Module

With continued reference to FIG. 1, after the vapors have been collected and concentrated by the sorbent tubes, they are thermally desorbed into the detection module 140. The detection module 140 analyzes the sample, and determines if any chemical agent is present. In one embodiment, the detection module 140 includes a chemical detector 141. The capability of the detection module 140 to detect explosives and/or LVPCs is dependent on the concentration of the chemical agent delivered to the detector 141, and the detection limit of the chemical detector 141. The chemical detector 141 may use a variety of technologies or combinations thereof for the detection and identification of chemical agent.

Examples of the detection technologies include, but are not limited to, mass spectrometry (MS), ion mobility spectrometry (IMS) and surface acoustic wave (SAW) sensors, Raman spectroscopy, infrared spectroscopy (IRS), gas chromatography (GC), Fourier transform infrared spectrometry (FTIRS), photoacoustic infrared spectroscopy (PAIRS), in-flame photometry (IFP), photo ionization detectors (PIDs), electrochemical sensors, and thermoelectric conductivity sensors.

A mass spectrometer detects and identifies chemicals by measuring the mass-to-charge ratio of charged particles. A typical mass spectrometer is comprised of three parts: an ion source, a mass analyzer, and a detector. The ion source subjects a sample of material with an electrical charge that causes the material to emit ionized particles. These particles are then moved as a gas to the separator or mass analyzer. Types of ion sources include electrospray ionization and matrix-assisted laser desorption ionization. The mass analyzer is the most flexible part of the mass spectrometer. Since an electric field will deflect charged particles, and the energy potential can be converted to inertial movement based on the mass and the potential, the mass analyzer uses these facts to steer certain ions to the detector based on their mass-over-charge ratios (m/z) by varying the electrical field potentials. It can be used to stabilize a narrow range of m/z or to scan through a range of m/z to catalog the ions present. The detector simply records the charge induced when an ion passes by or hits a surface. If a scan is conducted in the mass analyzer, the charge induced in the detector during the course of the scan will produce a mass spectrum, a record of the m/z's at which ions are present.

An ion mobility spectrometer (IMS) detects and identifies chemicals based upon the differential migration of gas phase ions through a homogeneous electric field. Specifically, an IMS system measures how fast a given ion moves in a uniform electric field through a given atmosphere. The molecules of the sample need to be ionized, usually by corona discharge, atmospheric pressure photoionization (APPI), electrospray ionization (ESI), or a radioactive source, e.g. a small piece of $^{63}$Ni or $^{241}$Am. In specified intervals, a sample of the ions is let into a drift chamber; the gating mechanism is based on a charged electrode working in a similar way as the control grid in triodes works for electrons. For precise control of the ion pulse width admitted to the drift tube, more complex gating systems such as a Bradbury-Nielsen design are employed. Once in the drift tube, ions are subjected to a homogeneous electric field ranging from a few volts per centimeter up to many hundreds of volts per centimeter. The electric field drives the ions through the drift tube where the ions interact with the neutral drift molecules contained within the system. Ions are recorded at the detector in order from the fastest to the slowest, generating a response signal characteristic for the chemical composition of the measured sample. IMS may be coupled with MS where both size and mass information may be obtained simultaneously.

Surface Acoustic Wave (SAW) sensors detect changes in the properties of acoustic waves as the waves travel at ultrasonic frequencies in piezoelectric materials. The piezoelectric materials are coated with materials capable of selectively adsorb chemical vapors. The acoustic waves interact with the absorbed chemicals and give characteristic responses that can be used to identify the chemicals. SAW sensors are typically used in arrays with multiple coatings. Pattern recognition algorithms are used to provide the means to identify agent classes and reject interferant responses that could cause false alarms.

GC can be used to detect a variety of chemical agents. Vaporized sample is swept onto a chromatographic column by the inert carrier gas and serves as the mobile phase. After passing through the column the solutes of interest generate a signal for a recording device to read. Like MS, GC also offers high sensitivity and specificity in detecting chemical agent in many sample forms. Samples separated by GC may be further analyzed by MS in a GC/MS detection system. GC may also be coupled with FTIRS. FTIRS is a technique that can identify compounds that are separated by gas chromatography. After the separation of the compounds, the sample passes through a light pipe where an infrared (IR) beam is passed through it. The adsorption of the IR energy is monitored as the signal is continuously scanned. Scans are collected on each peak and the signals are then manipulated with a Fourier transform that enhances the signal to noise ratio of the spectra taken.

Raman spectroscopy is based upon the interaction between optical radiation and various chemical species present in a sample. When the sample is irradiated with optical radiation a fraction of the optical radiation is scattered by the molecules in the sample.
The scattered radiation differs from the wavelength of the initial radiation by an amount proportional to the vibrational modes within the target molecules. The difference between the scattered radiation and incident beam, termed the Raman shift, corresponds to molecular vibrations in the target molecule. The degree of Raman shift is dependent upon the chemical structure of the molecules causing the scattering. During irradiation, the spectrum of the scattered radiation is measured with a spectrometer. In a preferred embodiment, the detection method is fiber optic Raman spectroscopy. In another embodiment, the spectroscopic interrogation unit 130 is an Ahura hand held Raman FirstDefender system (Ahura Corporation, Wilmington, Mass.).

IRS identifies chemical agent based on its adsorption spectrum in the intrared (IR) region of the electromagnetic spectrum. Characteristic vibrational wavelengths of most CWAs occur in the IR region. When infrared radiation passes through a gas or vapor, or is reflected off a surface (diffuse reflection), adsorption of radiation occurs at specific wavelengths that are characteristic of the vibrational structure of the gas molecules. Routine IR instruments measure the amount of light absorbed at a specific wavelength to look for a characteristic chemical group, such as the phosphorus-oxygen bond of nerve agents. More sophisticated instruments scan regions of the IR spectrum to generate a "fingerprint" pattern for individual chemicals.

As in IRS, PAIRS uses selective adsorption of infrared radiation by the target agent vapors to identify and quantify the agent present. A specific wavelength of infrared light is pulsated into a sample through an optical filter. The light transmitted by the optical filter is selectively adsorbed by the gas being monitored, which increases the temperature of the gas as well as the pressure of the gas. Because the light entering the cell is pulsating, the pressure in the cell will also fluctuate, creating an acoustic wave in the cell that is directly proportional to the concentration of the gas in the cell. Two microphones mounted inside the cell monitor the acoustic signal produced and send results to the control station.

FID operates by burning an sample in a hydrogen-rich flame. The compounds present emit light of specific wavelengths in the flame. An optical filter is used to let a specific wavelength of light pass through it. A photosensitive detector produces a representative response signal. Since most elements will emit a unique and characteristic wavelength of light when burned in this flame, this device allows for the detection of specific elements.

PID operates by passing the air sample between two charged metal electrodes in a vacuum that are irradiated with ultraviolet radiation, thus producing ions and electrons. The negatively charged electrode collects the positive ions, thus generating a current that is measured using an electrometer-type electronic circuit. The measured current can then be related to the concentration of the molecular species present.

Electrochemical sensors function by quantifying the interaction between an analyte's molecular chemistry and the properties of an electrical circuit. Fundamentally, electrochemistry is based on a chemical reaction that occurs when the target agent enters the detection region and produces some change in the electrical potential. This change is normally monitored through an electrode. A threshold concentration of agent is required, which corresponds to a change in the monitored electrical potential. This sensor technology provides a wide variety of possible configurations.

Thermoelectric conductivity sensors identify chemical agents by measuring the electrical conductivity of a surface material that absorbs the chemical agents. The electrical conductivity of certain materials can be strongly modulated following surface adsorption of various chemicals. Heated metal oxide semiconductors and room-temperature conductive polymers are two such materials that have been used commercially. The change in sensor conductivity can be measured using a simple electronic circuit, and the quantification of this resistance change forms the basis of sensor technology.

In one embodiment, the chemical detector 141 is a mass spectrometer. Mass spectrometers generally have a lower false positive rate than IMS and SAW detectors.

Command and Control Module

With continued reference to FIG. 1, the command and control module 150 provides coordination and control of the components in the chemical agent detection system 100. The command and control module 150 is designed to: (a) provide a single user interface to the entire chemical agent detection system 100; (b) allow a user to quickly determine the status of all components associated with the system; and (c) accept input to change parameters which allow for the configuration changes. At its most basic level, the command and control module 150 provides an alarm when a target chemical agent is identified by the detection module 140.

In one embodiment, the command and control module 150 comprise a memory 152, a controller 154 and an external port 156. The memory 152 may be used to store libraries of spectrometry finger prints of chemical agents and operation software. In one embodiment, the memory 152 is a flash memory. The controller 154 monitors and controls the operation of the chemical agent detection system 100 and provides an interface to the user about the status of the overall system. For example, the controller 154 may stage the timing, temperature and air flow rate of the sample collection module 110, and compare the results from the detection module 140 with the libraries of spectrometry finger print of chemical agents in the memory 152 to identify the target agent and reduce false positives.

In one embodiment, the controller 154 is a small, lightweight and available as a standard commercial off-the-shelf (COTS) product. In another embodiment, the controller 154 is a COTS offering and is packaged as a microbox PC with a passive PCI bus backplane. This configuration allows the component modularity for easy upgrades as computer hardware technologies improve. In another embodiment, the controller 154 is reside on a single board computer (SBC) that already have its peripheral interfaces built in: PCI bus, Ethernet, and RS-232 serial. Flash memory and DRAM can be sized to the control system requirements with removable memory sockets on the SBC. Communication from the controller 154 to the other components of the chemical agent detection system 100 is handled by COTS data acquisition, digital input/output, and analog input/output circuit cards that are PCI bus compatible.

In another embodiment, field-programmable gate array (FPGA) technology is used for monitors and control circuits in order to keep the weight, size, and especially power consumption at a minimum. The FPGA technology also affords minimum hardware redesign impact when implementing system upgrade.

The external port 156 is used for downloading software upgrades to the memory 152 and performing external troubleshooting/diagnostics.

Communication Module

With continued reference to FIG. 1, the communication module 160 maintains the communication between the chemical agent detection system 100, the other chemical detection systems, the regional command and control center that monitors all the chemical detection systems, and/or the local/state/federal authorities through cable or wireless connection.

Power Module

With continued reference to FIG. 1, the power module 170 provides power to the chemical agent detection system 100. In one embodiment, the power module 170 includes a long-life battery or batteries that can be recharged and reused. Preferably, the batteries are interchangeable with batteries from other Northrop Grumman portable systems. In another embodiment, the power module 170 includes an emergency generator. In another embodiment, the power module 170 includes a solar panel.

Figure 2:
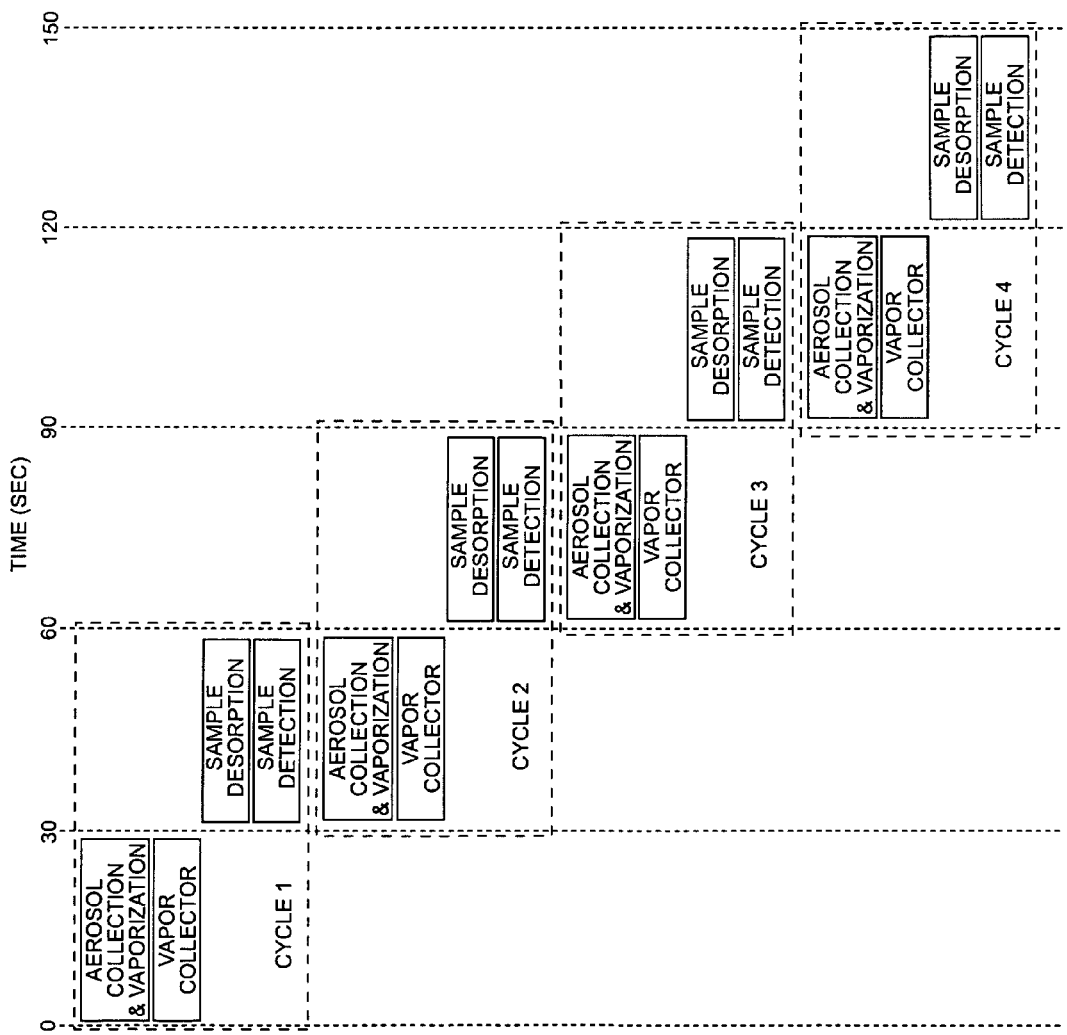

In one embodiment, the chemical agent detection system 100 is designed to autonomously collect both ambient vapor and aerosol samples, analyze, and report the results in 60 seconds. An exemplary timing of the collection and analysis cycles are outlined in FIG. 2. Aerosol sampling/vaporization and vapor collection occur in parallel for the first 30 seconds of the sampling/analysis cycle. Once the aerosols and vapors have been collected, they are desorbed and analyzed by the detector. This process takes an additional 30 seconds. The total time to result for the system is 60 seconds. In parallel with the desorption and detection of the first sample, a second sample is taken using the aerosol collector and the second sorbent tube. This overlap in system processing allows the unit to produce results every 30 seconds during normal operation, providing a near real-time monitoring capability.

Figure 3:
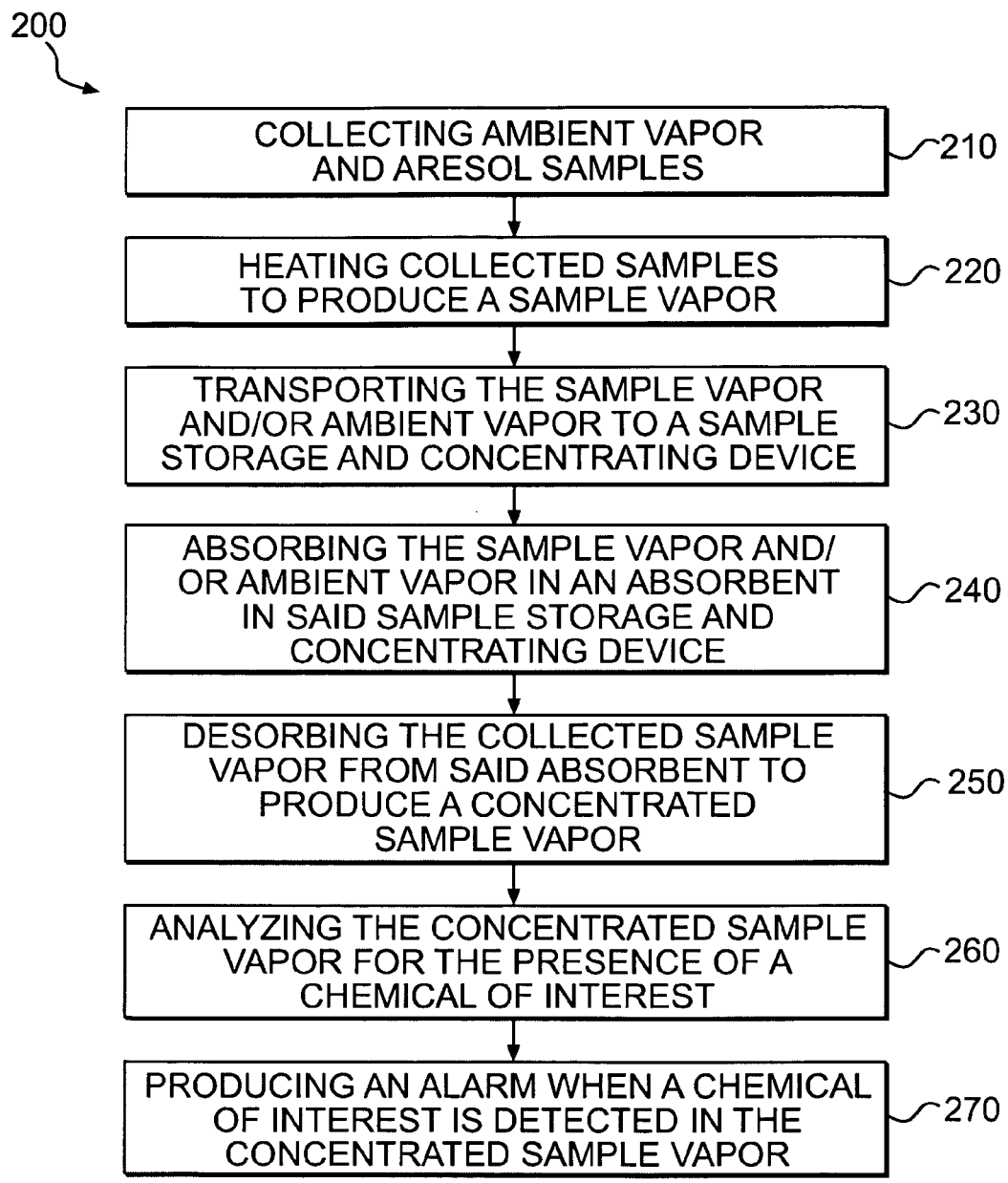

Also disclosed is a method for detecting a chemical of interest at a remote site. An embodiment of the method is shown in FIG. 3. The method 200 includes collecting (210) vapors, aerosols and particles from a fluid sample at a remote site, heating (220) the collected sample to produce a sample vapor, transporting (230) the sample vapor over a distance to a sample storage and concentrating device, absorbing (240) the transported sample vapor in an absorbent in the sample storage and concentrating device, desorbing (250) the absorbed sample vapor to produce a concentrated sample vapor, and analyzing (260) the desorbed sample vapor for the presence of the chemical of interest, and producing (270) an alarm if the chemical of interest is detected in the desorbed sample vapor sample. The method 200 may be performed using the system 100 as described above.

In one embodiment, the method 200 further includes collecting an ambient vapor and transporting the ambient vapor to the sample storage and concentrating device.

In another embodiment, the sample storage and concentrating device contains multiple sorbent tubes to allow parallel processing of multiple sample vapors.

EXAMPLES

The following specific examples are intended to illustrate the collection and detection of representative chemicals using methods and devices described in the embodiments. The examples should not be construed as limiting the scope of the claims.

Example 1

Detection of the Low Vapor Pressure Simulants (Vapor Pressure=$10^{-4}$ Torr) Using the Chemical Sample Collection and Detection System (CSCDS)

A. Experimental Setting

Figure 4:
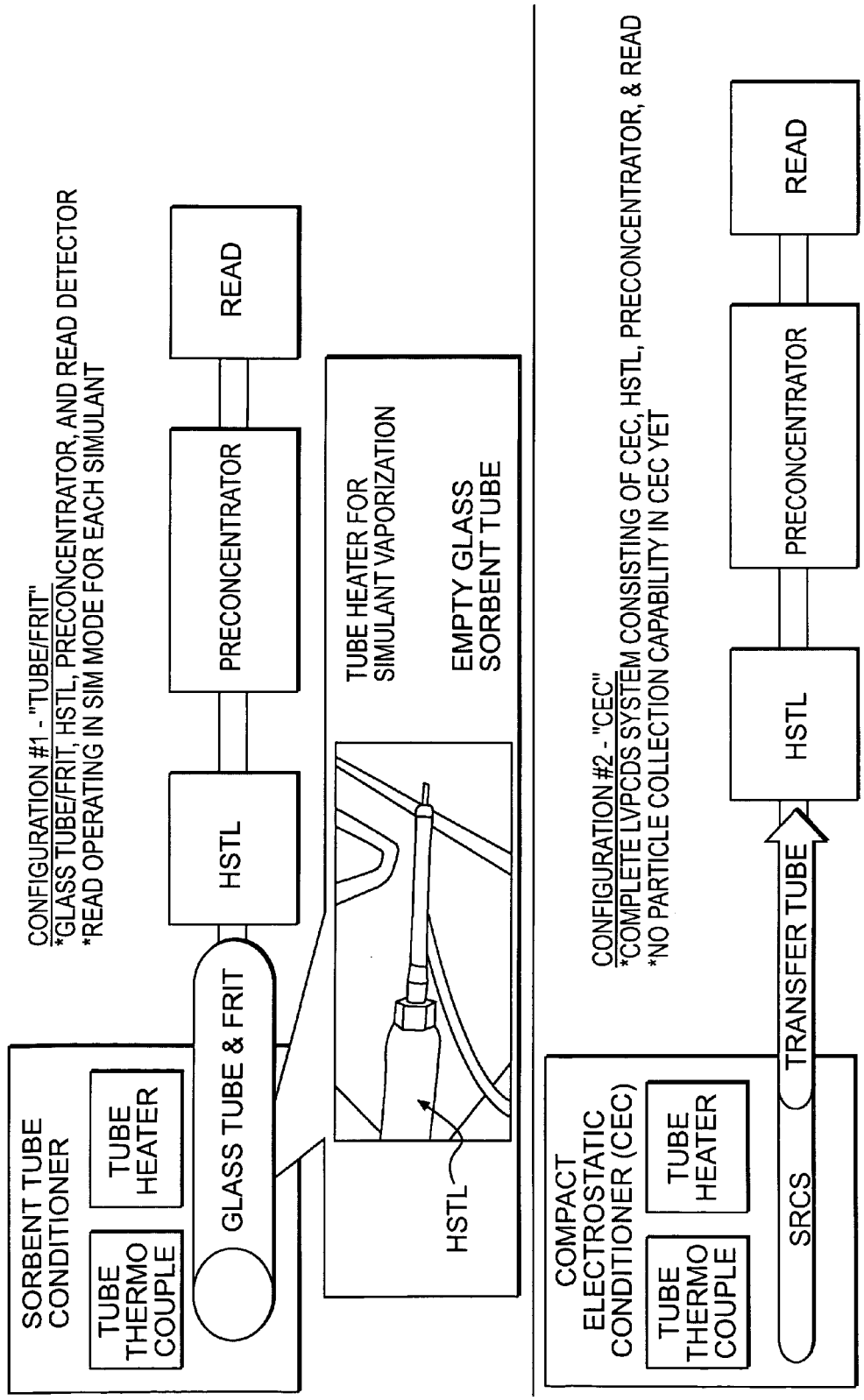

Testing of the CSCDS was done using two different sample introduction configurations that are shown in FIG. 4. In both configurations the sample transfer/preconcentration/analysis portion of the system are the same, only the sample introduction method is different. In configuration #1, a glass tube with a glass frit is used for sample introduction. Configuration #1, shown in the top panel of FIG. 4 allows the controlled introduction of different masses of simulant into the CSCDS. The sample, dissolved in a solvent (methanol for dimethoate and methamidophos or acetone for acephate), is placed onto the glass frit using a microliter syringe. This enables placement of a precise volume of a known concentration of simulant onto the glass flit so that the mass of simulant is known and the simulant concentration can be calculated. The glass tube/frit is placed onto the end of the HSTL using a standard Swagelok fitting with a Teflon ferrule. A heating sleeve, which is part of a commercial sorbent tube conditioner, is then placed over the glass tube/frit. A Dynatherm sampling pump is started, then the sorbent tube conditioner is turned on and the temperature of the glass tube/frit increased to 300° C. The sample is transferred through the HSTL and collected onto a Dynatherm sorbent tube and then the glass tube/frit is cooled. Background samples are run after each sample run using the same procedures except no sample is loaded onto the glass frit. The sample collected in the Dynatherm sorbent tube is re-vaporized and transferred to the READ (Reverse Electron Attachment Detector) through a heated transfer line for the detection of simulants.

The second CSCDS configuration (#2) replaces the glass tube/frit sample introduction setup with an compact electrostatic compactor (CEC) (Sceptor Industries, Inc. Kansas City, Mo.). This setup tests the capability of the CEC to vaporize the sample and transfer it through the CSCDS for detection. In the second configuration, a microliter syringe is used to place a known mass of simulant (in solvent) onto the Solid Radial Collector Surface (SRCS) in the CEC. Once the sample is placed into the SRCS the Dynatherm sampling pump is started and the SRCS is heated to 300° C. The vaporized sample transferred through the HSTL and collected by the Dynatherm. A background sample is run using no simulant after the CEC is cooled to be sure the CSCDS is clear of sample and ready for another run. The sample collected in the Dynatherm sorbent tube is re-vaporized and transferred to the READ through a heated transfer line for the detection of simulants.

B. Results (1) Detection of Simulants Through HSTL—Sample Introduction Configuration #1

Figure 5:
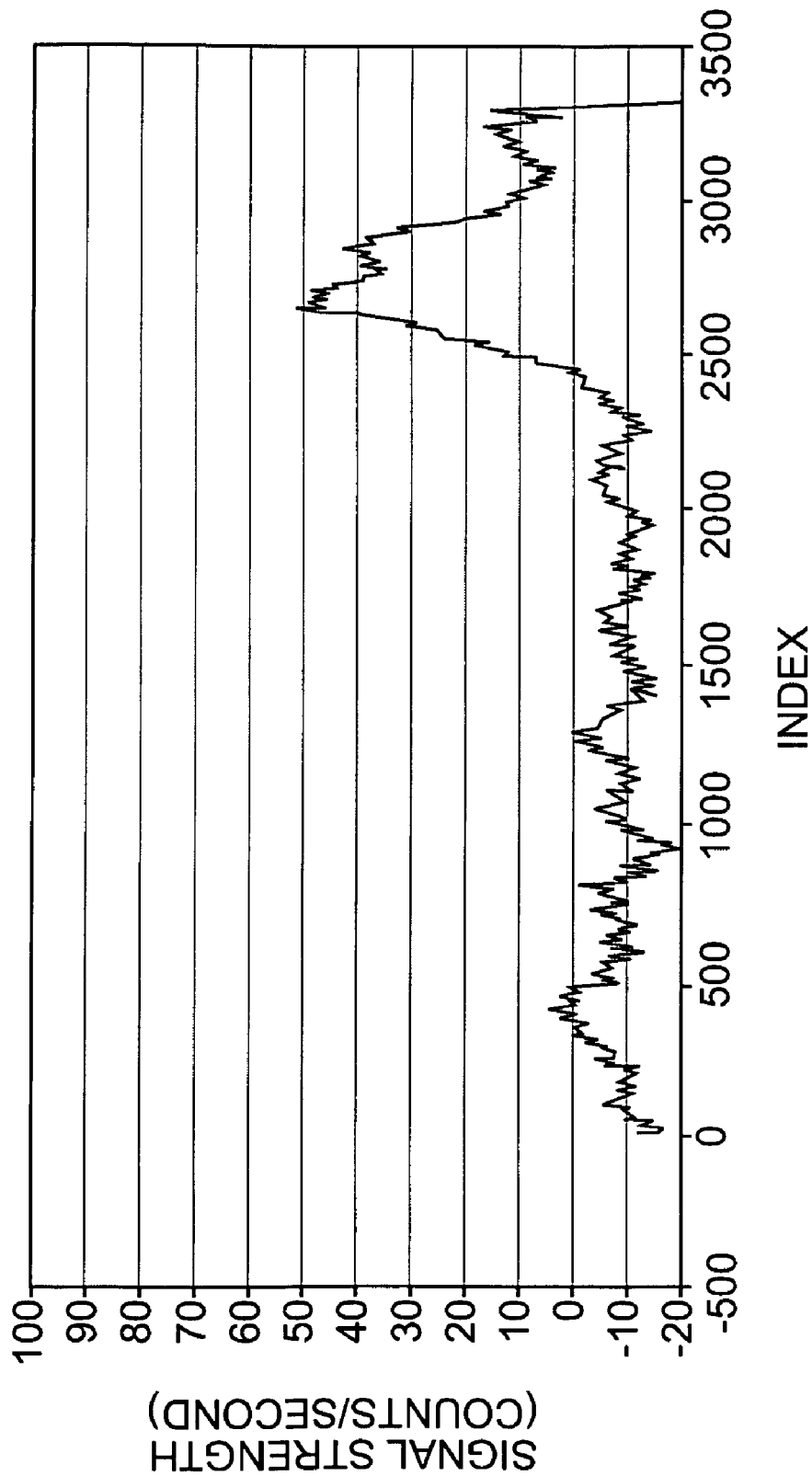
Figure 6:
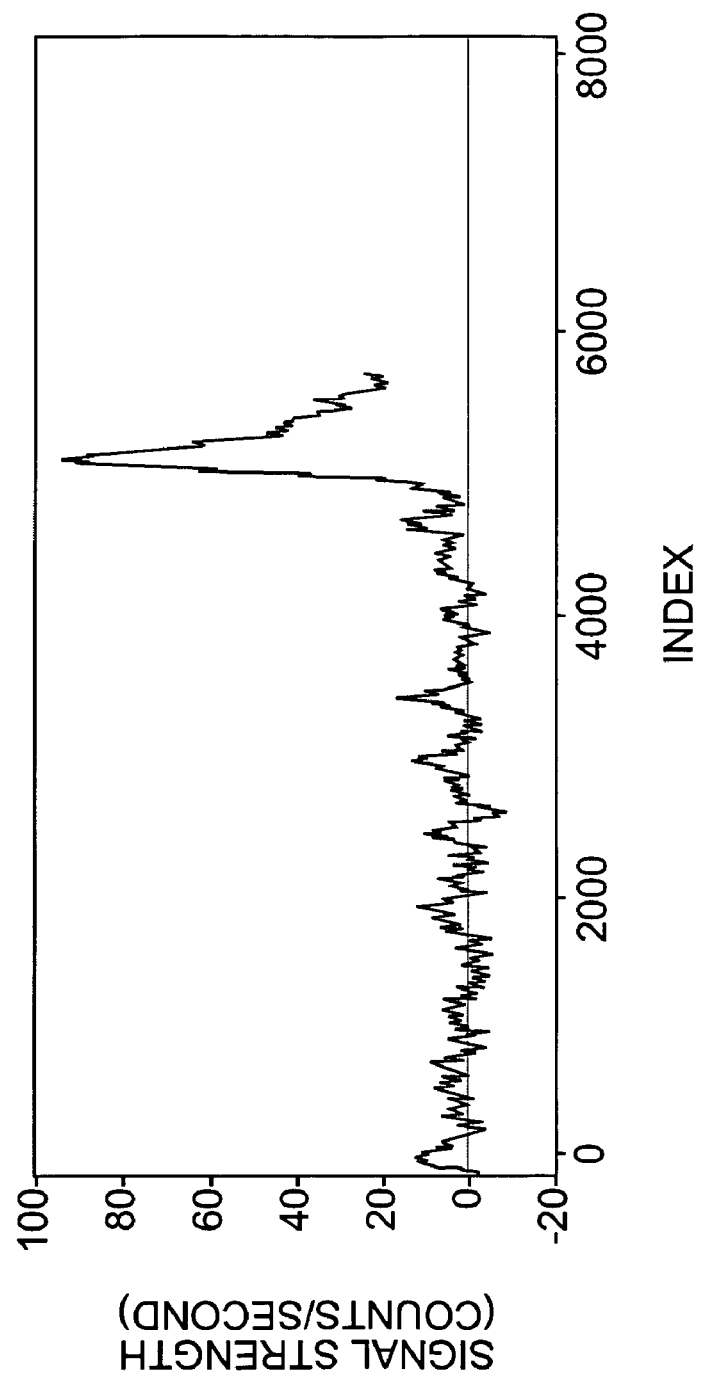
Figure 7:
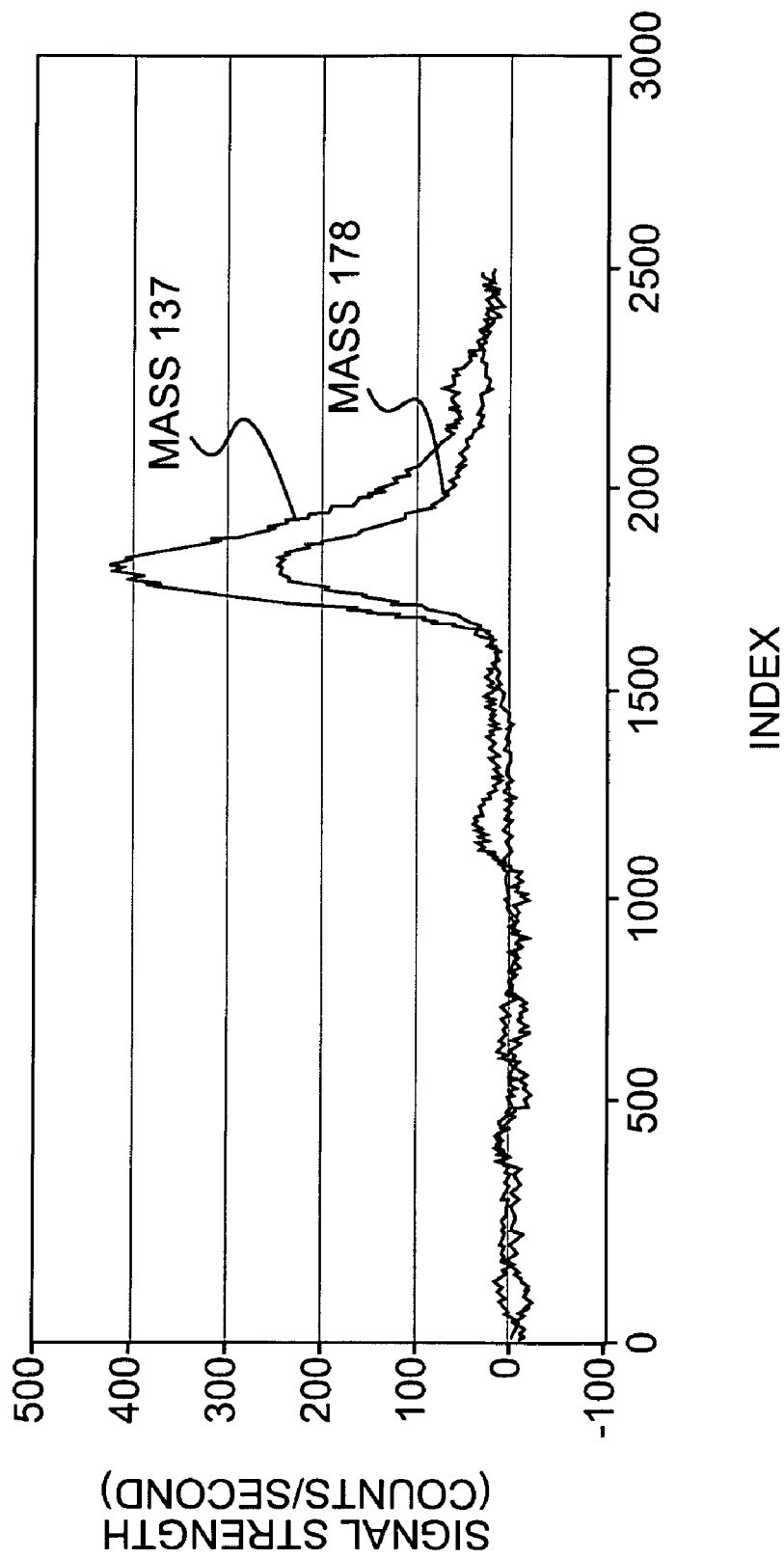

The first series of experiments on the CSCDS demonstrated successful detection of the three simulants dimethoate, methamidophos, and acephate. A 3-ft HSTL was used for dimethoate and methamidophos, and a 10-ft HSTL was used for acephate. FIG. 5 shows the signal for dimethoate through the 3-ft HSTL. The dimethoate vapor was generated using experimental configuration #1 where a solution of known concentration was injected onto the glass frit. Based on the sampling flow rate of the CSCDS this signal corresponds to 0.43 parts-per-billion (ppb), or 430 parts-per-trillion (ppt), of dimethoate vapor. This result clearly demonstrates that the CSCDS is capable of detection of ppb levels of low vapor pressure chemicals. FIG. 6 shows the CSCDS response for methamidophos. The CSCDS signal is produced from 3,880 ng of methamidophos, which corresponds to a concentration of 286 ppb. This result once again demonstrates the CSCDS capability to detect ppb levels of low vapor pressure chemicals. FIG. 7 shows the CSCDS signal for acephate transferred through 10 feet of HSTL. This figure shows the signal produced by introduction of 1000 ng of acephate, which corresponds to a concentration of 134 ppb of acephate. The signals for both mass 137 and mass 178 of acephate at ppb levels demonstrate the capability of the CSCDS for detection of a third low vapor pressure chemical at ppb levels through a 10 ft long HSTL.

As summarized in Table 1, the CSCDS is capable of detecting dimethoate at a concentration of 9 ppl (particles-per-liter), methamidophos at a concentration of 3529 ppl, and acephate at a concentration of 909 ppl.

TABLE 1

Mass Simulant Detected and the Number of Particles Corresponding to the Detected Mass

|  | Mass Simulant Detected (ng) | Number of Particles | Threat Concentration Detected (ppl) |
|---|---|---|---|
| Dimethoate | 10 | 218 | 9 |
| Methamidophos | 3880 | 84689 | 3529 |
| Acephate | 1000 | 21827 | 909 |

(2) Probability of False Alarm for Dimethoate and Acephate

The CSCDS will preferably exhibit false alarm rates of <1%. All false alarm testing was performed using CSCDS configuration #1 and a 3 ft silcosteel HSTL at a temperature of 180° C. The testing schedule, shown in Table 2, includes background testing, sample testing and cleaning of the system. Background testing consists of the tests run without any sample placed into the glass tube/frit. Sample testing consists of placing sample onto the glass frit and running the CSCDS to acquire a signal from the sample. The cleaning protocol removes residual sample that can result in background signal. A cleaning protocol that consists of a 10 minute sampling time through the HSTL onto the sorbent tube, and a 10 minute transfer time from sorbent tube to focusing trap was determined through experimentation. This protocol removes all residual LVPC in the CSCDS and provides a clean background.

TABLE 2

False Alarm Testing Schedule

| Day 1 | Day 2 | Day 3 | Day 4 |
|---|---|---|---|
| Background | Background | Clean | Clean |
| Background | Background | Sample | Background |
| Background | Sample | Background | Background |
| Sample | Clean | Background | Background |
| Clean | Background | Background | Background |
| Background | Sample | Background | Sample |
| Background | Clean | Background | Clean |
| sample | Background | Background | Sample |
| Clean | Background | Sample | Clean |
| Background | Background | Clean | Background |
| Background | Background | Background | Background |
| Background | Sample | Sample | Background |
| Background | Clean | Clean | Sample |
| Background | Backgound | Background | Clean |
| sample | Backgound | Background | Background |
| Clean | Backgound | Background | Background |
| Background | Sample | Sample | Background |
| Sample | Clean | Clean | Background |
| Clean | Sample | Sample | Background |
| Background | Clean | Clean | Sample |
| Background | Background | Background | Clean |
| Background | Background | Background | Background |
| Background | Background | Background | Background |
| Sample | Sample | Sample | Background |
| clean | Clean | Clean | Background |

Table 3 shows the results of the testing for the probability of false alarm for both dimethoate and acephate. Testing was performed using laboratory air with no special precautions to keep out any environmental background that might contain interferents. Therefore, this test does reflect one proposed concept of operations where the CSCDS operates in a building protection mode drawing in conditioned room air. The results for dimethoate show a 0% probability of false alarm at a concentration of 0.92 ppb (920 ppt) and for acephate a probability of false alarm of 0% at a concentration of 61 ppb.

TABLE 3

Probability of False Alarm Results for Dimethoate and Acephate

| Simulant | Concentration, ppb | $P_{FA}$ (%) | Test runs |
|---|---|---|---|
| Dimethoate | 0.55 | 1.6 | 62 |
|  | 0.94 | 0.0 |  |
| Acephate | 61 | 0.0 | 42 |
|  | 122 | 0.0 |  |

Example 2

CSCDS Detection of Aerosolized Simulants

Figure 8:
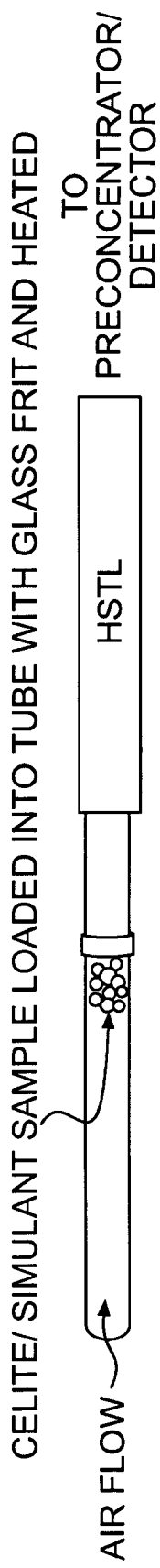

To demonstrate the CSCDS capability to detect aerosols, configuration #1 was used with a 10-ft HSTL (silcosteel tube). The sample introduction setup is shown in FIG. 8 with the aerosol simulant placed on the opposite side of the glass frit from the HSTL. As in previous experiments, a heating sleeve is placed over the glass tube/frit containing the simulant/Celite and heated to 300° C. while the Dynatherm draws air through the sample. The heating and sampling times are the same as previous experiments. The aerosol simulants used in this test were prepared to contain 100 ppm (w/w) of each LVPC simulant supported on silica particulates.

Figure 9:
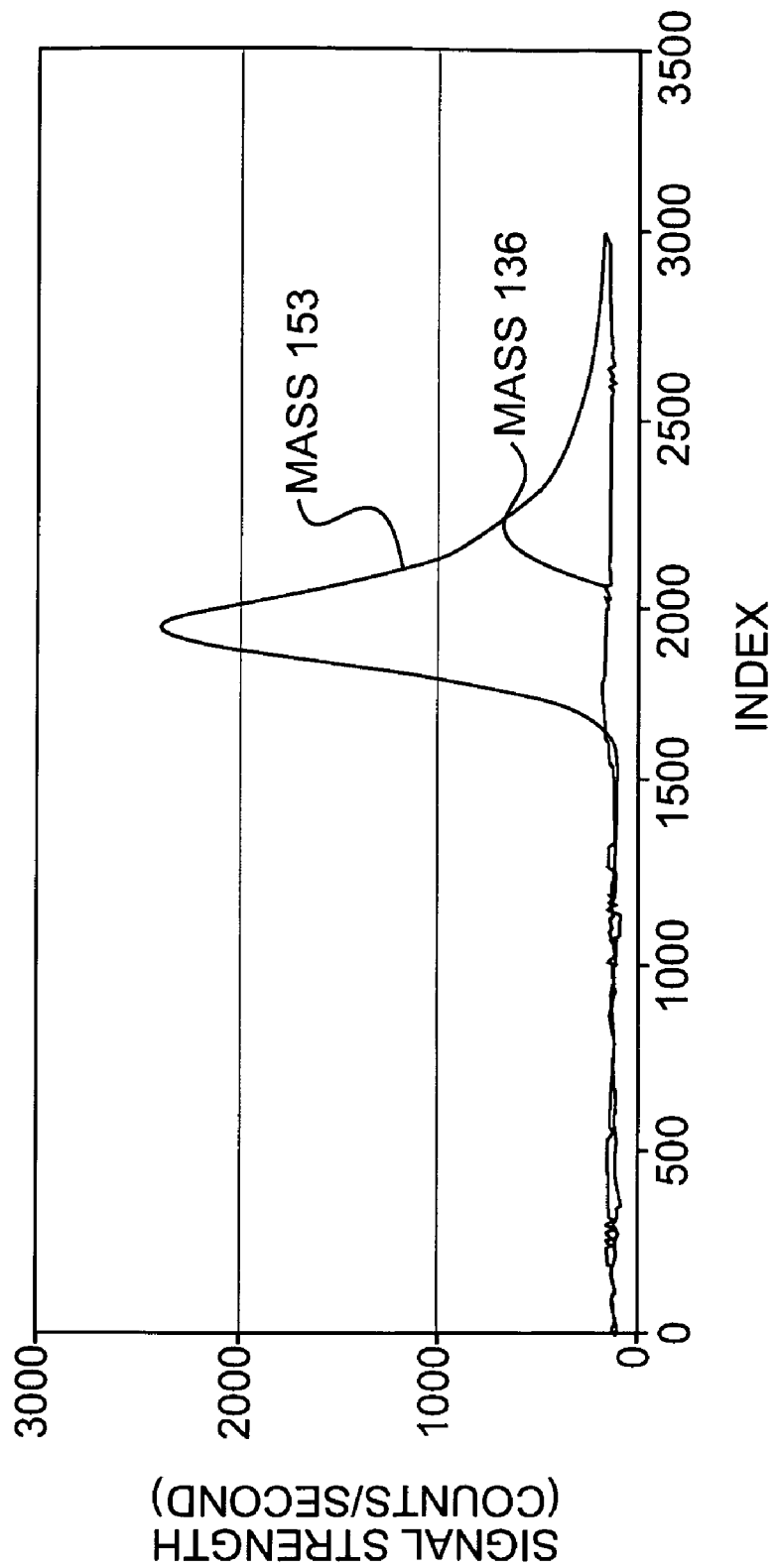
Figure 10:
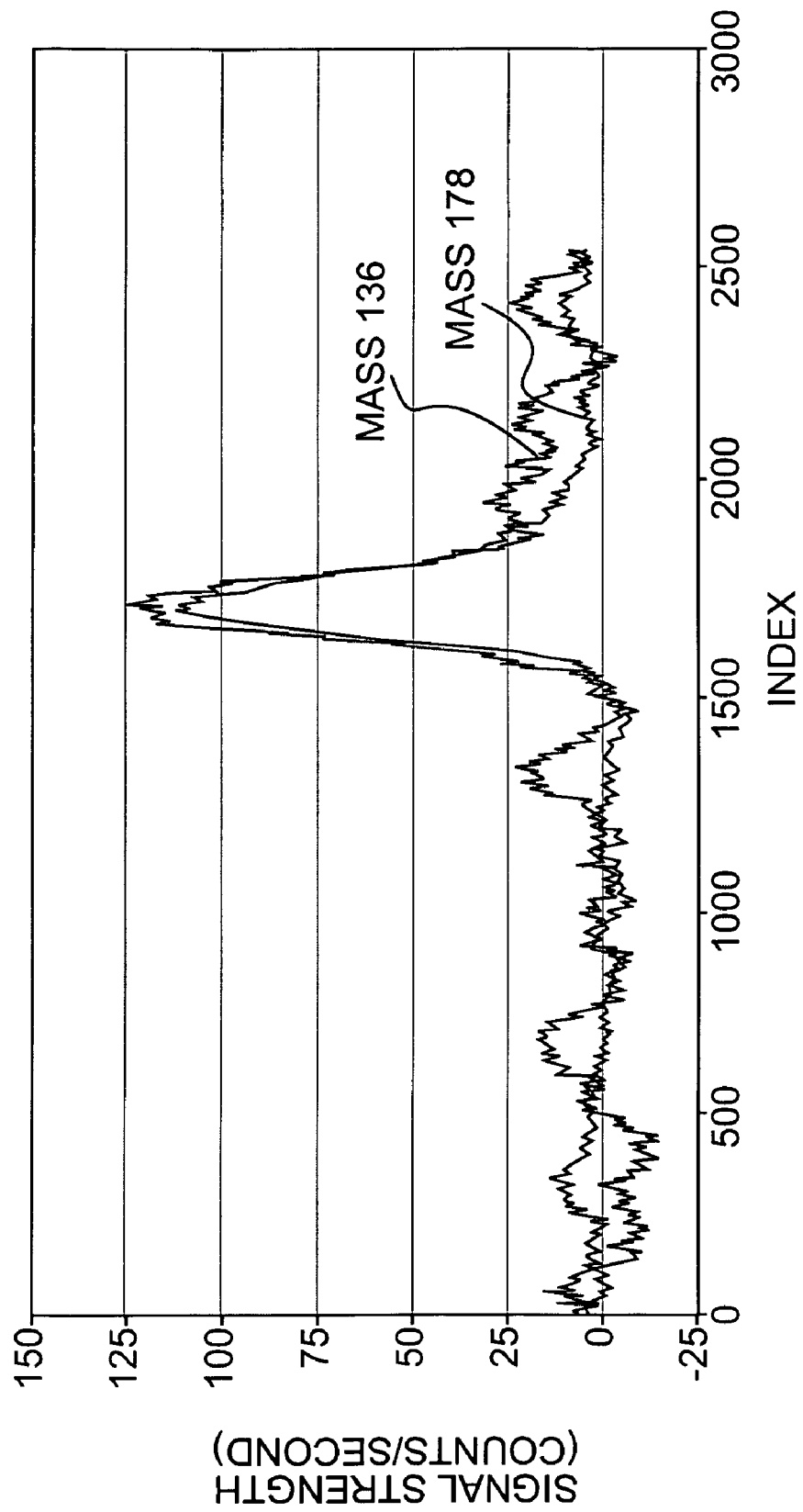

The response of the CSCDS to dimethoate aerosol and acephate aerosol through a 10-ft HSTL are shown in FIGS. 9 and 10. The data demonstrates that the simulants supported on Celite can be thermally vaporized in air and carried down the 10-ft HSTL in air and detected by the CSCDS. This proves that the original concept of the CSCDS to capture aerosols, vaporize them, and transfer them down an HSTL is feasible.

Comparison of the two different plots also demonstrates the selectivity of the system. In the dimethoate case two masses, 136 amu and 153 amu, are monitored. Mass 136 amu does not exhibit a response to dimethoate as expected, however the acephate plot shows that mass 136 amu and mass 178 amu both show a strong response, which is expected based on early studies of the simulant properties when ionized and detected by the READ detector.

Example 3

CSCDS Full System Testing

This series of tests demonstrates that the full CSCDS operates as predicted with all sub-components integrated into the system. The complete CSCDS includes a CEC, a HSTL, a preconcentrator (Dynatherm) and a READ detector. The CEC was tested for its ability to vaporize sample into a 3-ft silcosteel HSTL. The HSTL is connected to a Dynatherm vacuum line, a mass spectrometer turbo and roughing pumps. A heated transfer line, covered in aluminum foil, connects the Dynatherm to the mass spectrometer. The heat transfer line is heated using heat tape and insulated with glass wool to keep the line temperature uniform. The glass wool is covered with aluminum foil to protect the insulation. The heat transfer line temperature was constant at 200° C. over the course of all experiments. The READ sample introduction module was also covered with glass wool insulation and kept at 200° C.

A Experimental Setting

The operating parameters of the individual components of the CSCDS were optimized by adjusting the temperature and flow rates for each component to maximize the signal strength. A significant level of effort was devoted to the determination of the best temperature settings and flow rates used throughout the system to generate the maximum signal. The CEC temperature was set such that the temperature at the midpoint of the solid radial collector surface (SRCS) was 350° C. This temperature setting was a result of numerous experiments using configuration #1 (glass tube/frit) to determine the best thermal desorption temperature of the simulants. A series of experiments reveals that the optimum location for sample placement on the SRCS was on the tip. The silcosteel HSTLs operated at 200° C., the Teflon HSTLs operated at 80° C. The silcosteel lines are adjustable to different temperatures; however, the manufacturer recommended keeping the temperature at or below 200° C. The Dynatherm thermal desorption temperatures for both sorbent tube and focusing trap desorption temperatures was 300° C. The internal silcosteel tubing in the Dynatherm was operated at the maximum allowable temperature, 200° C.

B. Results

1. Detection of Dimethoate Through a 3-ft HSTL

Figure 11:
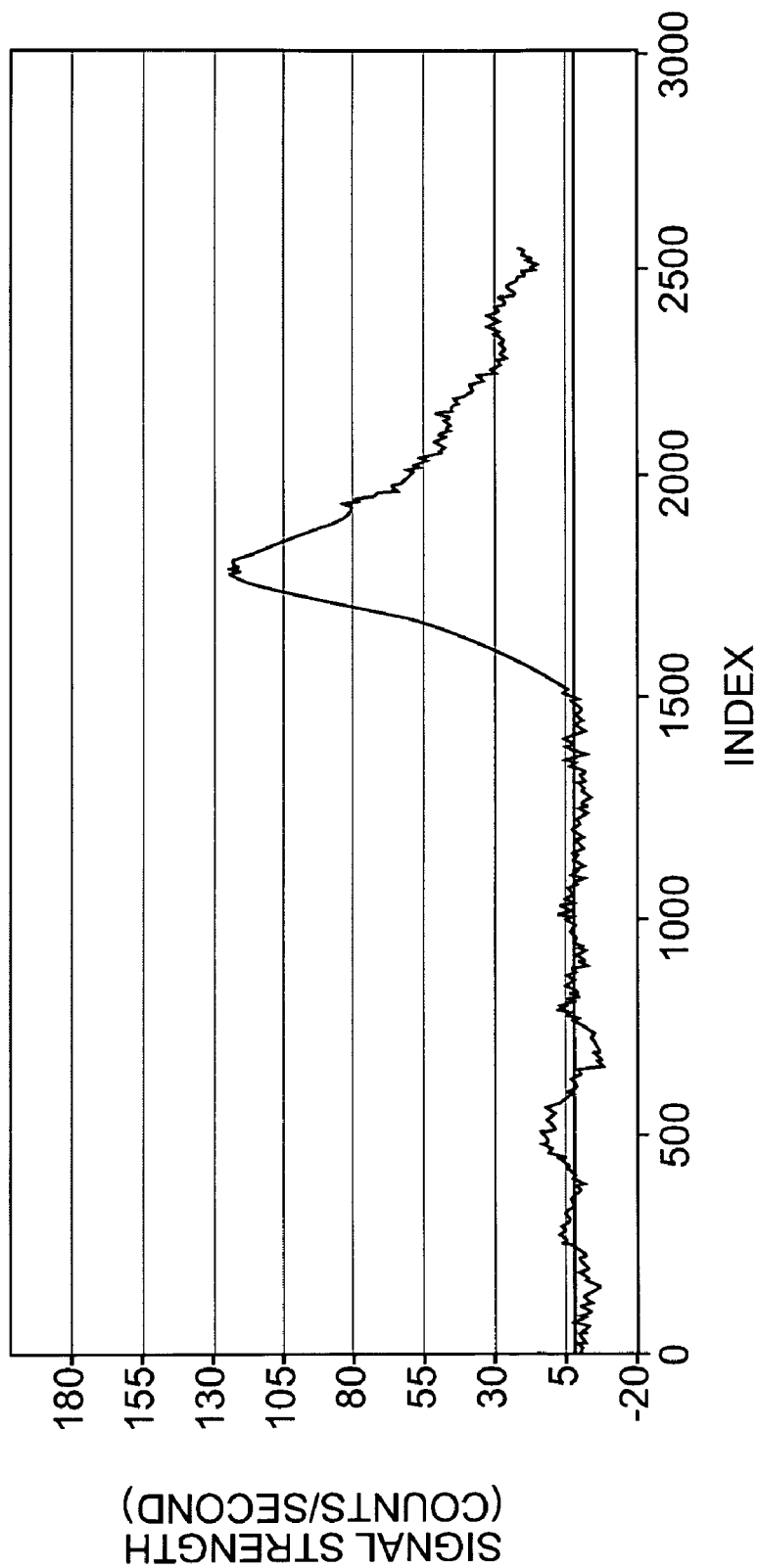

The 3 ft silcosteel HSTL was used first to determine the capability of the CSCDS to detect the dimethoate through the minimum length of HSTL available. A known volume of a standard solution of dimethoate was spotted onto the tip of the SRCS (250 ng) and the SRCS heated to 350° C. At the same time, the Dynatherm sampling pump started so that the Dynatherm was sampling throughout the heating schedule of the SRCS. During this time the Dynatherm collected the sample, the SRCS was ramped to a temperature of 350° C. and held there for 2 minutes. Dynatherm sampling was stopped at 2 minutes and the SRCS temperature ramped down to ambient. The response of the CSCDS, shown in FIG. 11, clearly shows good signal strength for dimethoate. It is important to note that the concentration of dimethoate in the experiment, based on sample flow rates through the CSCDS is 11 ppb. Therefore the experiment demonstrates that the CSCDS is capable of detecting ppb levels of the simulant dimethoate through a 3 ft HSTL.

2. Detection of Dimethoate, Methamidophos, and Acephate Through a 10-ft HSTL

Figure 12:
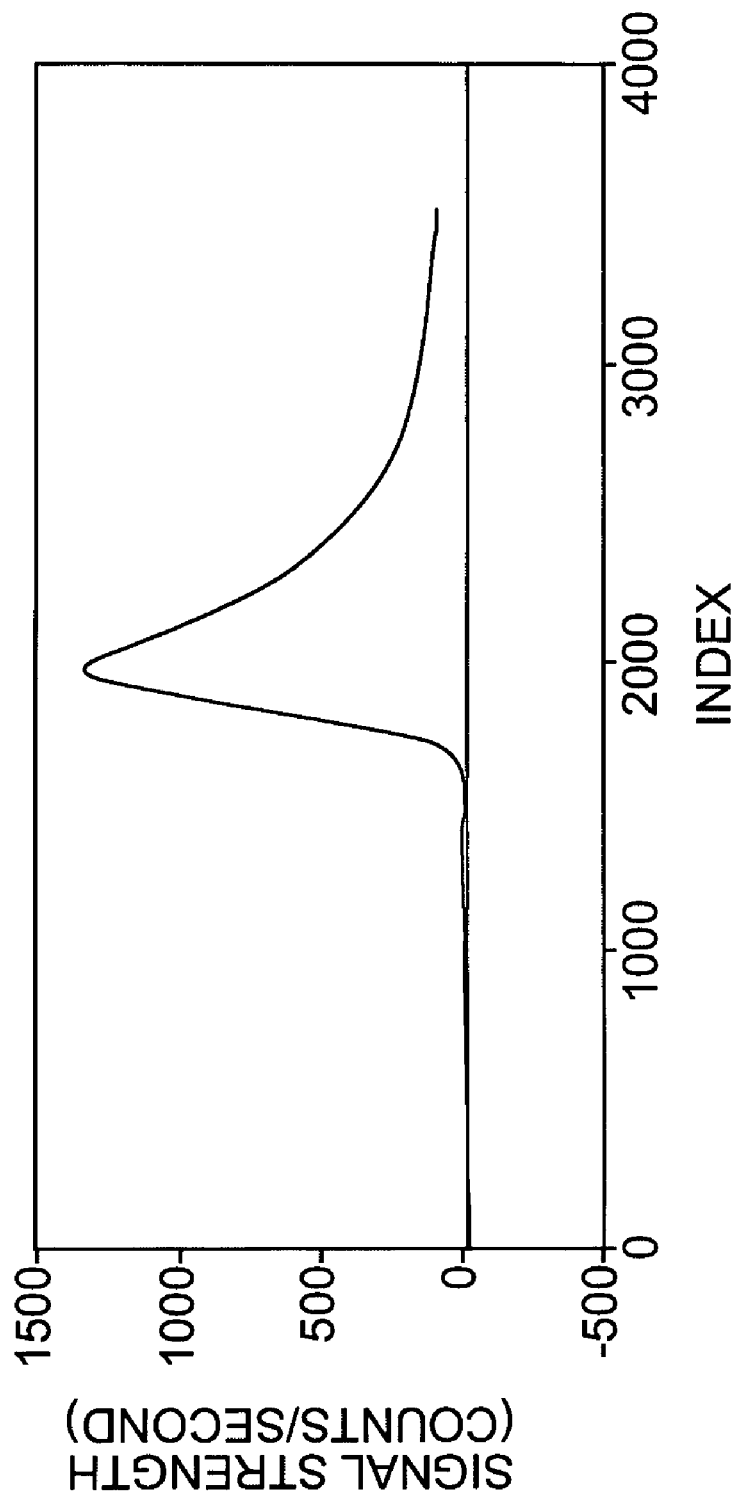

Once the CSCDS demonstrated its capability to detect dimethoate through a 3-ft HSTL the same experiment was performed through the 10 foot long silcosteel HSTL for all three simulants. Results for dimethoate are shown in FIG. 12 with the 10-ft HSTL operating at 200° C. The concentration of dimethoate in the experiment is 195 ppb and the signal strength is good. This data clearly shows that the LVPCDS is capable of detecting ppb levels of dimethoate through 10-ft of HSTL meeting the DHS requirements for ppb level detection at a distance from the detector.

Figure 13:
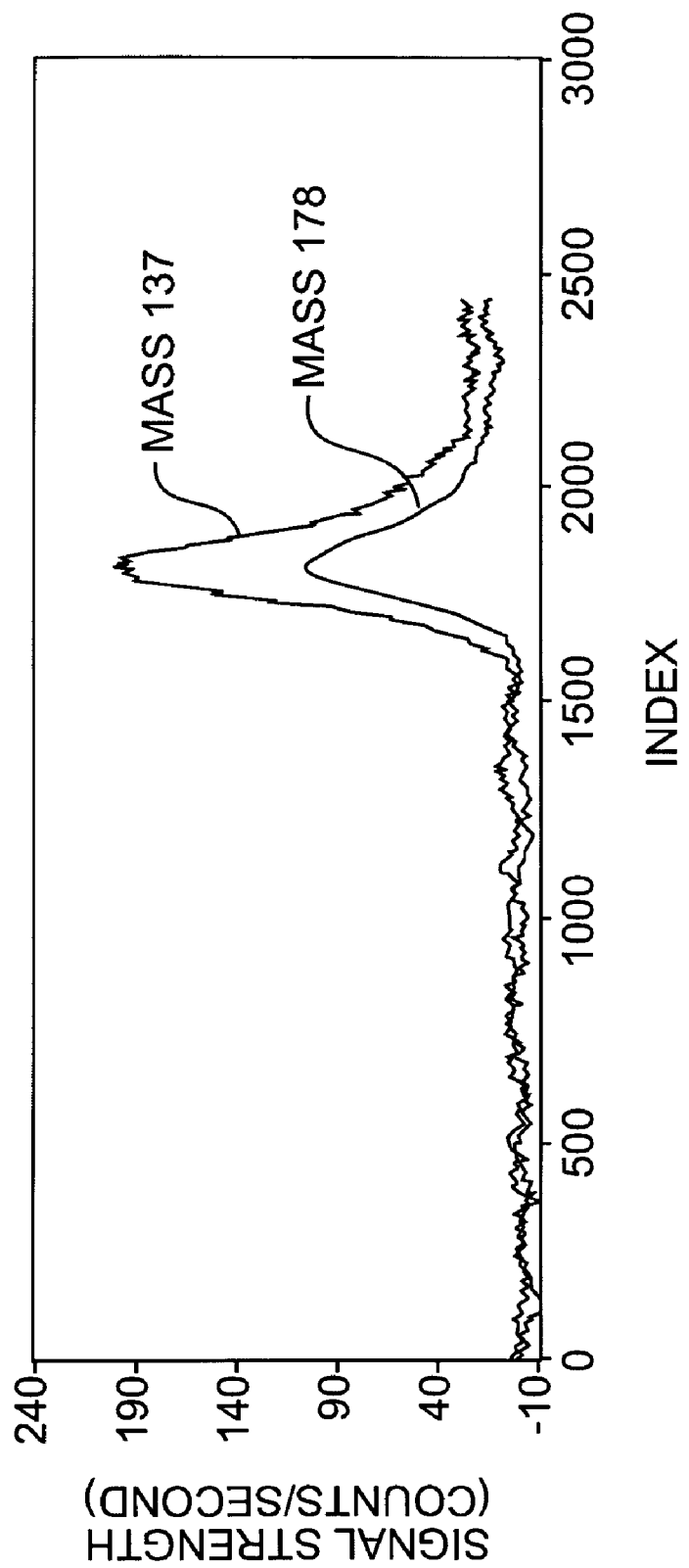

FIG. 13 shows the CSCDS response to 800 ppb of acephate through the 10-ft silcosteel HSTL. As in the case of dimethoate, the signal strength is strong and the LVPCDS demonstrates the capability to detect ppb levels of acephate through 10 ft of HSTL. It is worthwhile noting that the system detects two signals corresponding to two different mass peaks for acephate at 137 amu and 178 amu demonstrating the selective nature of the system.

Figure 14:
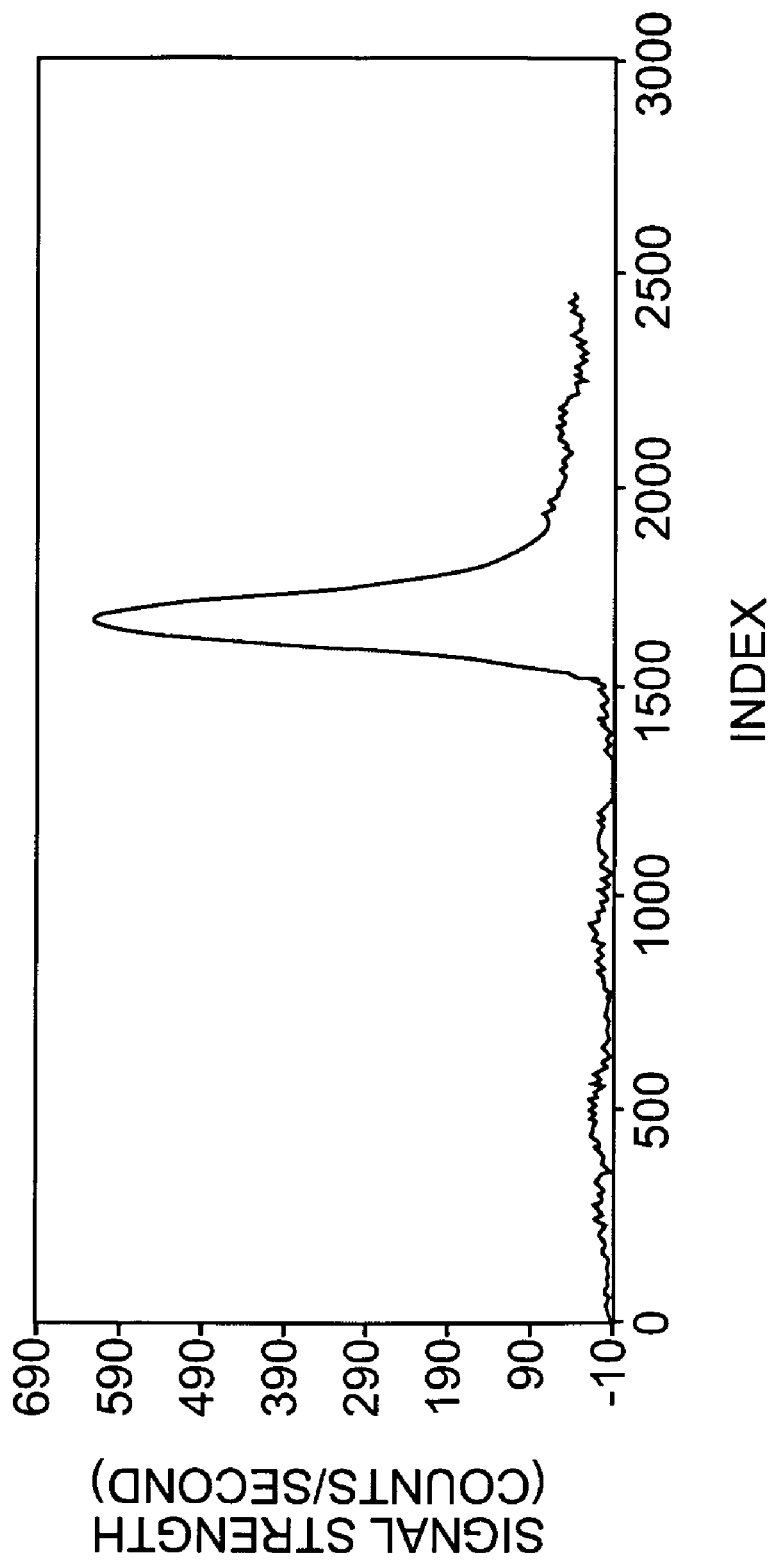

FIG. 14 shows the response of CSCDS to methamidophos. The experiment was run using the same parameters as dimethoate and acephate. The concentration of methamidophos in this example is 8 ppm and the signal strength is good. This concentration does not represent the detection limit of the CSCDS for methamidophos, however, based on experience it is likely that the detection limit is in the high ppb level.

The Examples above demonstrate that the CSCDS is capable of detecting ppb levels for 2 of the three LVPC simulants through 3-ft and 10-ft HSTLs. Data shows the CSCDS capable of detecting ppb to ppm levels of dimethoate, acephate, and methamidophos over 10 ft of HSTL. Calculations suggest that at operational threat levels the system could detect the release of an LVPC at a distance of 60 feet. False alarm data demonstrated that the CSCDS exhibits a $P_{FA}<1.0\%$ for ppb concentrations of dimethoate and acephate. A summary of the experimental results showing the detection capabilities of the LVPCDS and the detection subsystem are presented in Table 4.

TABLE 4

Summary of experimental results for the NGC-LVPCDS

| Simulant | Detector Detection Limit, ppb | CSCDS-CEC Detection Limit | CSCDS Demonstrated Detection Limit, ppb | HSTL Length, ft |
|---|---|---|---|---|
| Dimethoate | 0.33 | | | 0 |
| | | 0.43 | | 3 |
| | | | 11** | 3 |
| | | | 195** | 10 |
| Methamidophos | 146 | | | 0 |
| | | 268 | | 3 |
| | | | 8000** | 10 |
| Acephate | 19 | | | 0 |
| | | 134** | 800** | 10 |

**Actual measurement concentration not detection limit

The CSCDS also detects the simulants dimethoate and acephate supported on a silica substrate, the combination being a dusty agent simulant. Data in Table 5 show that the simulants on Celite were successfully detected over an HSTL distance of 10 feet with good signal to noise.

TABLE 5

CSCDS Detection of the Simulants Supported on the Substrate Material Celite Over a ten-feet Distance

| Simulant | Mass Celite/Simulant (mg) | Signal Max. | SNR | HSTL Length, (ft) |
|---|---|---|---|---|
| Dimethoate/Celite | 12.1 | 151 | 35 | 10 |
| Methamidophos/Celite | — | ND | — | 10 |
| Acephate/Celite | 7.4 | 53 | 12 | 10 |

The foregoing discussion discloses and describes many exemplary methods and embodiments of the present invention. As will be understood by those familiar with the art, the invention may be embodied in other specific forms without departing from the spirit or essential characteristics thereof. Accordingly, the disclosure of the present invention is intended to be illustrative, but not limiting, of the scope of the invention, which is set forth in the following claims.

What is claimed is:

1. A system for remote detection of a chemical, comprising:
    a sample collection module that collects a sample and produces a sample vapor at a first location;
    a sample delivery module that delivers said sample vapor from said first location to a second location;
    a sample storage and concentration module that collects said sample vapor at the second location; and
    a sample analysis module that analyzes the sample collected in the sample storage and concentration module.

2. The system of claim 1, wherein said sample delivery module delivers said sample vapor through a first heated sample transfer line (HSTL).

3. The system of claim 1, wherein said a sample analysis module comprises a chemical detector that detect said chemical of interest using a technology selected from the group consisting of mass spectrometry (MS), ion mobility spectrometry (IMS) and surface acoustic wave (SAW) sensors, Raman spectroscopy, infrared spectroscopy (IRS), gas chromatography (GC), Fourier transform infrared spectrometry (FTIRS), photoacoustic infrared spectroscopy (PAIRS), in-flame photometry (IFP), photo ionization detectors (PIDs), electrochemical sensors, and thermoelectric conductivity sensors.

4. The system of claim 1, further comprising a power module.

5. The system of claim 1, further comprising a communication module.

6. The system of claim 1, further comprising a command and control module.

7. The system of claim 6, wherein said command and control module comprises a memory, a controller, and a external port.

8. The system of claim 1, wherein said sample collection module comprises an aerosol/particle collector and a heater.

9. The system of claim 8, wherein said sample vapor is produced by heating the aerosols and particles collected by the aerosol/particle collector.

10. The system of claim 8, wherein said sample collection module further comprises an ambient vapor collector that collects an ambient vapor at the first location.

11. The system of claim 8, wherein said sample delivery module also delivers the ambient vapor collected at the first location to the sample storage and concentration module.

12. The system of claim 1, wherein said sample concentration module comprises at least one sorbent tube that collects the sample vapor delivered from said sample delivery module.

13. The system of claim 12, wherein said sample concentration module comprises two sorbent tubes.

14. The system of claim 12, wherein said sample concentration module comprises three sorbent tubes.

15. A method for detecting a chemical at a remote site, comprising:
    collecting aerosols and particles from a fluid sample at said remote site;
    heating the collected aerosols and particles to produce a sample vapor;
    transporting the sample vapor over a distance to a sample storage and concentrating device;
    absorbing the transported sample vapor in an absorbent in the sample storage and concentrating device;
    desorbing the absorbed sample vapor, and
    analyzing the desorbed sample vapor for the presence of said chemical.

16. The method of claim 15, further comprising:
    producing an alarm when said chemical is detected in said desorbed sample vapor.

17. The method of claim 15, wherein said sample vapor is transported via a heated sample transfer line (HSTL).

18. The method of claim 15, wherein said sample storage and concentrating device comprises at least two absorbent tubes to allow parallel processing of multiple vapor samples.

19. The method of claim 15, further comprising:
    collecting an ambient vapor sample at said remote site, and transport the collected ambient vapor to said sample storage and concentrating device.

20. The method of claim 19, wherein said sample vapor and said ambient vapor are transported to said sample storage and concentrating device via different heated sample transfer lines.

* * * * *